United States Patent [19]

Rosensweig et al.

[11] Patent Number: 4,668,379

[45] Date of Patent: May 26, 1987

[54] PROCESS FOR MAGNETICALLY STABILIZING A FLUIDIZED BED CONTAINING NONMAGNETIZABLE PARTICLES AND A MAGNETIZABLE FLUID

[75] Inventors: Ronald E. Rosensweig, Summit; George Ciprios, Pittstown, both of N.J.

[73] Assignee: Exxon Research and Engineering Company, Florham Park, N.J.

[21] Appl. No.: 737,243

[22] Filed: May 23, 1985

[51] Int. Cl.[4] .......................... B03C 1/24; B01D 15/02
[52] U.S. Cl. .................................... 208/157; 210/656; 208/310 Z; 34/1; 55/3; 585/825; 585/828
[58] Field of Search ............... 208/164, 310 Z, 310 R; 34/1, 10; 55/3, 67, 100, 386, 390; 209/1, 38, 40, 212, 172.5; 210/661, 656, 695, 196; 423/DIG. 16; 585/820, 821, 828, 825

[56] References Cited

U.S. PATENT DOCUMENTS

| | | | |
|---|---|---|---|
| 2,882,244 | 4/1959 | Milton | 252/455 |
| 3,130,007 | 4/1964 | Brek | 23/113 |
| 3,439,899 | 4/1969 | Hershler | 259/1 |
| 3,440,731 | 4/1969 | Tuthill | 34/1 |
| 3,483,969 | 12/1969 | Rosensweig | 209/1 |
| 3,686,343 | 8/1972 | Bearden, Jr. et al. | 260/674 |
| 3,793,385 | 2/1974 | Bond et al. | 260/674 |
| 3,951,785 | 4/1976 | Kaiser et al. | 209/1 |
| 4,085,037 | 4/1978 | Quets et al. | 209/1 |
| 4,115,927 | 9/1978 | Rosensweig | 34/1 |
| 4,132,005 | 2/1979 | Coulaloglou | 34/10 |
| 4,136,016 | 1/1979 | Rosensweig | 208/34 |
| 4,143,469 | 3/1979 | Kamholz | 34/1 |
| 4,247,987 | 2/1981 | Coulaloglou | 55/3 X |
| 4,274,987 | 6/1981 | Augustyn | 260/23 |
| 4,292,171 | 9/1981 | Mayer et al. | 208/164 |
| 4,294,688 | 10/1981 | Mayer | 208/164 |
| 4,319,892 | 3/1982 | Waghorne et al. | 55/60 |
| 4,319,893 | 3/1982 | Hatch et al. | 55/60 |
| 4,443,231 | 4/1984 | Siegell | 55/3 |

FOREIGN PATENT DOCUMENTS

1148513 4/1969 United Kingdom.
1597617 9/1981 United Kingdom.

OTHER PUBLICATIONS

V. A. Naletova, "Stabilization of Bubble-Liquid Processes by an Electric Field" 1982, 5-12, Izvestiya Akademii Nauk SSSR, Mekhanika Zhidkosti i Gaza.
M. Filipov, "Conf. on Theoretical and Applied Magnetic Hydrodynamics" 1962, 139-140, Zvest. Akad. Nauk. Latviishoi.
S. Ergun, "Fluid Flow Through Packed Columns", 1952, 89, Chemical Engineering Process.
R. E. Rosensweig, "Magnetic Stabilization of the State of Uniform Fluidization" 1979, 260-269, American Chemical Society.
R. E. Rosensweig, "Fluidization: Hydrodynamic Stabilization with a Magnetic Field", 1979, 57-60, Science.
M. K. Bologa et al "The Influence of an Electromagnetic Field on the Structural-Hydrodynamic Properties of a Fluidised Bed", 41-48..
D. G. Ivanov et al, "Ammonia Synthesis on a Catalyst Fluidized in a Magnetic Field", 1971, 1006-1010, Kinetika i Kataliz.
D. G. Ivanov et al, "Determination of the Critical Fluidization Velocity of an Iron—Chromium Catalyst Bed in a Magnetic Field" 1971, 2224-2227—Zhurnal Prikladnoi Khimii.

*Primary Examiner*—Glenn Caldarola
*Attorney, Agent, or Firm*—E. Thomas Wheelock

[57] ABSTRACT

This invention relates to a fluidized bed process. More particularly, the present invention is a process for operating a magnetically stabilized fluidized bed by using a magnetizable fluid to fluidize solid particulate nonmagnetizable fluidizable particles. The operating conditions are such that there is substantially no random motion or time-varying pressure fluctuation as measured at a point within the bed.

12 Claims, 6 Drawing Figures pages
PROCESS FOR MAGNETICALLY STABILIZING A FLUIDIZED BED CONTAINING NONMAGNETIZABLE PARTICLES AND A MAGNETIZABLE FLUID

FIELD OF THE INVENTION

This invention relates to a fluidized bed process. More particularly, the present invention is a process for operating a magnetically stabilized fluidized bed by using a magnetizable fluid to fluidize solid particulate nonmagnetizable fluidizable particles. The operating conditions are such that there is substantially no random motion or time-varying pressure fluctuation as measured at a point within the bed.

Such a magnetically stabilized medium has features of an expanded fixed bed; there is no gross solids backmixing and very little or no fluid bypassing. A bed of the magnetically stabilized particles shares many qualities of the normal fluidized bed in that the pressure drop through the bed is no larger than the value at incipient fluidization; and, continuous solids throughput is permitted. Beds of the magnetically stabilized media also share some of the qualities of a fixed bed, i.e., staged contacting can be readily achieved and fluid bypassing is either small or completely absent thereby making possible high conversions when operated as a chemical reactor, or high product recovery and purity when operated as a separation device. But magnetically stabilized media have the added unique feature that the included solids may be moved without longitudinal mixing. Concomitantly, particle mixing motion is nil and because the particles are levitated crushing forces are absent so there is low particle attrition.

The use of magnetizable fluidizing fluid permits the use of cheaper relatively available bed solids, e.g., zeolitic catalysts, and the processing of non-magnetic solids such as coal particles, oil shale particles, etc. Compared to a conventional magnetically stabilized fluidized bed, this invention circumvents the need to prepare solids having dual functions, e.g., particles which are both magnetic and catalytic. The fluid flowability range of these beds should be wider than with conventional magnetically stabilized beds (MSB) due to the absence of direct particle/particle magnetic attraction. The rheology, flowability, dispersion characteristics and other features of the beds are expected to differ from conventional MSB's.

BACKGROUND OF THE INVENTION

Many chemical and physical reaction processes such as hydrogenation, oxidation, polymerization, coating, filtering, adsorption, and the like are carried out in fluidized beds. A fluidized bed, briefly, consists of a mass of solid particulate fluidizable material in which the individual particles are neutrally levitated free of each other by fluid drag forces such that the mass or fluidized bed possesses certain characteristics of a liquid. Like a liquid, it will flow or pour freely, there is a hydrostatic pressure head, its surface seeks a constant level, it will permit the immersion of objects and will support relatively buoyant objects. A fluidized bed is conventionally produced by directing a flow of a fluid through a porous or perforated plate or membrane, underlying the particulate mass, at a rate sufficient to support the individual particles against the force of gravity. Conditions at the minimum fluidization flow, i.e., the incipient fluidization point, are dependent on many parameters including particle size, particle density, etc. Any increase in fluid flow beyond the incipient fluidization point causes an expansion of the fluidized bed to accommodate the increased fluid flow. Further increase of the gas velocity will produce a condition where the particles are then carried out of the apparatus, a condition otherwise known as entrainment.

Fluidized beds possess many desirable attributes, for example, they may be used to effect temperature control, heat transfer, catalytic reactions, and various chemical and physical reactions such as oxidation, reduction, drying, adsorption, polymerization, coating, diffusion, filtering and the like.

Numbers of workers have studied the influence of magnetization on the dynamics of gas fluidized solids wherein there is no net solids flow to or from the vessel, the so-called batch beds. An early account of this phenomena was reported by M. V. Filippov [*Applied Magnetohydrodynamics, Trudy Instituta Fizika Akad. Nauk., Latviiskoi SSR* 12: 215–236 (1960); *Zhurnal Tekhnicheskoy Fiziki*, 30 (9): 1081–1084 (1960); *Izvestiya Akad. Nauk.*, Latviiskoi SSR, 12(173): 47–51 (1961); *Izvestiya Akad. Nauk.: Latviiskoi SSR*, 12: 52–54 (1961); and Aspects of Magnetohydrodynamics and Plazma Dynamics, Riga (1962), *Izvestiya Akad. Nauk.*, Latviiskoi SSR, pp. 637 to 645]. Subsequent workers have reported on the influence that magnetization exerts on pulsations, heat transfer, structure, and other characteristics of magnetized and fluidized solids in batch beds. A review of some of this work is given by Bologa and Syutkin [*Electron Obrab Mater*, 1: 37–42 (1977)]. Ivanov and coworkers have described some benefits of using an applied magnetic field of fluidized ferromagnetic solids in the ammonia synthesis process [see British Pat. No. 1,148,513 and numerous publications by the same authors, e.g., Ivanov et al, *Kinet. Kavel*, 11(5): 1214–1219 (1970); Ivanov et al, *Zhurnal Prikladnoi Khimii*, 43, 2200–2204 (1970); Ivanov et al, *Zhurnal Prikladnoi Khimii*, 45: 248–252 (1972); Ivanov et al, *Chemical Industry*, 11; 856–858 (1974); Shumkov et al, *Zhurnal Prikladnoi Khimii*, 49 (11): 2406–2409 (1976)]. Various means for operating magnetic fields to stabilize the bed of magnetizable solids have been disclosed in U.S. Pat. Nos. 3,440,731; 3,439,899; 4,132,005 and 4,143,469 and Belgium Pat. No. 865,860 (published Oct. 11, 1978).

R. E. Rosensweig [Science, 204: 57–60 (1979), *Ind. Eng. Chem. Fundam.*, 18 (3): 260–269 (1979) and U.S. Pat. Nos. 4,115,927 (now reissued as Re. 31,439 on Nov. 15, 1983), and 4,136,016 (now Re. 31,186, reissued Mar. 22, 1983), the entirety of all are incorporated by reference] reported on a number of features of magnetically stabilized fluidized magnetizable solids and a systematic interpretation of the phenomena. In these publications and patents, R. E. Rosenweig reported on the quiescent fluid-like state for the magnetically stabilized fluidized bed (MSB), particularly one which is totally free of bubbles or pulsations or backmixing when a uniform magnetic field is applied to a bed of magnetizable solids, approximately colinear with the direction of the fluidizing gas flow.

Others have reported the use of continuously flowing cocurrent or countercurrent magnetically stabilized fluidized beds with a variety of chemical reactions and adsorptive or absorptive processes. U.S. Pat. No. 4,127,987 to Coulaloglou et al, issued Feb. 3, 1981, relates to a process for continuous countercurrent contacting to absorb one species from a contacting fluid by use of at least one magnetically stabilized fluidized bed. Similarly, U.S. Pat. No. 4,292,171, issued Sept. 29, 1981 and U.S. Pat. No. 4,294,688 to Mayer, issued Oct. 31, 1981, disclose catalytic hydrocarbon conversion processes in which magnetizable particles with or without separate catalytic particles are passed countercurrent to the hydrocarbon feed to effect a chemical conversion. U.S. Pat. No. 4,319,892 to Waghorne et al, issued Mar. 16, 1982, and U.S. Pat. No. 4,319,893 to Hatch et al, issued Mar. 16, 1982, teach an adsorption process for the separation of hydrogen from feed gas or vapor which contains hydrogen in admixtures of one or more hydrocarbon components. Each process uses a set of vertically stacked magnetically stabilized fluidized beds to effectuate one or more steps in the adsorption-desorption process. The adsorbent passes through each of the MSBs in a direction countercurrent to its particular gas flow.

V. A. Naletova in an article entitled "Stabilization of Bubble-liquid Processes by an Electric Field" in *Izvest. Akad. Nauk. SSR, Mekh, Zhio. Igaza*, No. 4, pp. 5–12 (1982) (Trans. Plenum Press (1983) 491–7) discusses the stabilization of bubbles rising or sediments descending in stagnant liquids where either phase may be more polarizable. Analogous magnetic stabilization is also discussed.

However, none of the noted publications suggest the use of magnetizable fluid as a medium for stably fluidizing nonmagnetizable particles.

The use of ferrofluids as the medium in which particles having different densities are separated by their densities is disclosed in U.S. Pat. No. 3,951,785 to Kaiser et al, issued Apr. 20, 1976, and in U.S. Pat. No. 3,484,969 to Rosenweig, issued Dec. 16, 1969. Neither of these patents describe a process using ferrofluid as a fluidizing medium for nonmagnetizable particles.

SUMMARY OF THE INVENTION

This invention relates to a process for fluidizing a bed of solid particulate, nonmagnetizable fluidizable material located within an external magnetic force field. Backmixing of solids is prevented. The portion of the bed containing the solid particulate material is subjected to a substantially uniform applied magnetic field having a substantial component along the axis of the bed. The bed containing the solid particulate nonmagnetizable fluidizable material is stably fluidized by the flow of magnetizable fluidizing fluid having a superficial fluid velocity which may be:

(a) more than $U_m$, the velocity at the onset of bed expansion, and (b) less than the superficial fluid velocity $U_t$ required to cause instability in the bed, as detected, for example, by the onset of magnetic field fluctuations during continuous fluidization in the presence of the applied magnetic field.

The strength of the magnetic field and its minimal orientational deviation from the bed axis are maintained to prevent or suppress random motion in the fluidized media at a given fluid flow rate and with selected fluidized particle makeup. The strength of the magnetic field may be a constant along the bed axis or it may be varied to create density variations along the bed length as a function of spatially varying magnetic field strength.

As a result of this process, backmixing of solids is suppressed or eliminated and the bed solids move through the fluidizing vessel in piston-like motion. This flow pattern of the solids is highly desirable for use in staged contacting operations.

This process may be used as the basis for other processes which involve the contacting of solids with liquids in reactors, separation processes, filtration processes, heat exchangers, ion exchangers, and related processes in which it is desired to efficiently transfer mass, heat, momentum, charge, or combination of these properties between phases.

DETAILED DESCRIPTION OF THE PREFERRED EMBODIMENTS

Figure 1:
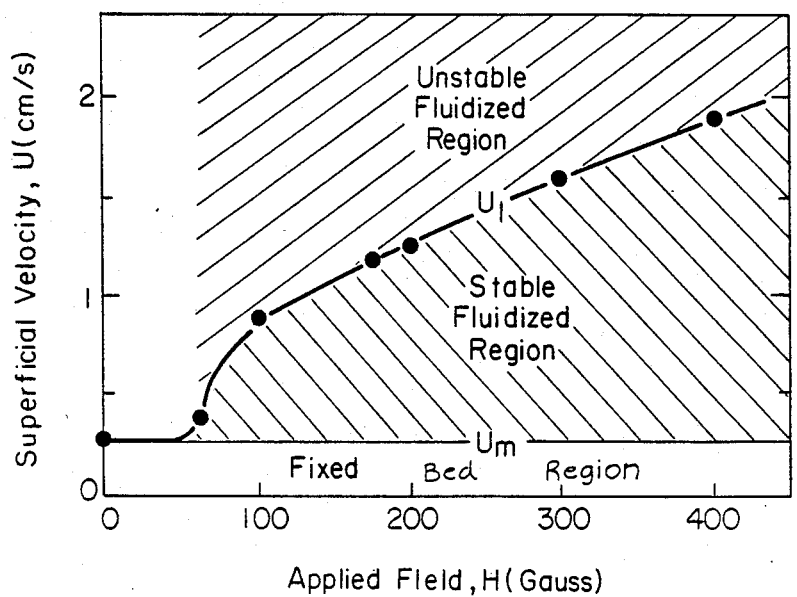
FIG. 1 shows experimental data in a graph of the velocities $U_m$ and $U_t$ of the fluidizing medium as a function of the intensity of a magnetic field applied to the fluidized bed. The graph shows a stable region of operation between $U_m$ and $U_t$ for the exemplified process.

As indicated previously, the present invention relates to a process for operating a stably fluidized bed for a range of fluid velocities while using a magnetizable fluid as a fluidizing medium and nonmagnetizable solids as the dispersed phase in the beds. Operation in this manner provides substantial absence of gross solids circulation, little or no fluid bypassing and little or no bed fluctuation of any kind. The fluid bed is stabilized by subjecting at least a portion of the fluidized bed comprising solid particulate nonmagnetizable fluidizable material and a magnetizable fluidizing fluid to an applied magnetic field having a substantial component along the axis of the fluidized bed. The magnetic field may be uniform along the length of the bed or nonuniform to vary the effective density of the bed as a function of the nonuniformity. As it will be seen from a description of the invention and reference to the drawings, the maximum superficial fluid velocity that can be employed while maintaining a stable non-fluctuating bed is a function of the axial component of magnetization. It is to be recognized that factors such as particle density, particle composition and shape, particle size, length and shape of the bed, etc., each affect the maximum fluidization velocity that can be achieved at a given component of magnetization. The variation and adjustment of these factors will be apparent to those skilled in the art and practicing the process of the present invention.

When fluid is passed upwardly through a bed of closely sized granular solids, a pressure gradient is required to overcome friction. In order to increase the rate of flow, a greater pressure gradient is required. When the pressure difference (also known as differential pressure or pressure drop ΔP) approaches the weight of the bed divided by the bed's cross-sectional area (expressed in comparable units), the solids begin to expand. This expansion of the solids is created at superficial fluid velocities far below the terminal free settling velocities of the solid particles and constitutes the beginning of fluidization. This point is often called the point of incipient fluidization. Thus, the normal minimum fluidization superficial fluid (gaseous or liquid) velocity is the fluid velocity observed when the pressure difference of the fluid passing through the fluidized bed, as measured between upper and lower surfaces of the bed, is first substantially the same as the bed weight per unit cross-sectional area. The superficial fluid velocity is the linear fluid velocity that would be measured in an empty vessel at the same throughput rate. It may be arrived at by dividing the volume of flow rate by the cross-sectional area of a particular vessel. This velocity may be measured in units of feet per second, centimeters per second, etc. This point of normal minimum-fluidization superficial fluid velocity, in the absence of an applied magnetic field, is the minimum fluidization superficial fluid velocity ($U_{mf}$) of the process of this invention.

The fluids used as fluidizing media in this invention are magnetizable in nature. This classification of materials includes paramagnetic salt solutions, e.g., concentrated aqueous manganese chloride, and, especially the various liquids known as ferrofluids. Ferrofluids are stable colloidal dispersions of superparamagnetic particles having a diameter of about 0.01 microns. These dispersions retain their liquid properties in a magnetic field. By proper choice of stabilizing agents, magnetic properties can be conferred on a wide range of liquids which include water, hydrocarbons, and fluorocarbons. These colloidal suspensions form an interesting class of magnetic liquids in which it is possible to induce substantial magnetic body forces. The suspended particles usually contain a single magnetic domain and are of such size that they do not settle under gravity or appreciably cluster even in the presence of a strong magnetic field. The magnetic response of a ferrofluid results from the coupling of individual particles with a substantial volume of the bulk liquid. This coupling is facilitated by a stabilizing agent which adsorbs on the particle surface and is also solvated by the surrounding liquid. The solvated layer is also in part responsible for the stability of the suspension.

The magnetic properties of the ferrofluid can be described by considering the particles in the ferrofluid to behave as an assembly of non-interacting magnets. Their magnetic properties have been successfully correlated by superparamagnetic theory, taking into account the composition, size distribution, volume concentration, and domain magnetization of the particles in suspension. In the absence of a magnetic field, the particles are randomly oriented and the ferrofluid has no net magnetization. In magnetic field, the particles tend to align with the field resulting in a net induced fluid magnetization. As the applied magnetization increases, a saturation value is closely approached. At saturation, the particle moments are all aligned in the direction of the applied field. As soon as the magnetic field is removed, the particles rapidly become randomly oriented again because of thermal fluctuations. The ferrofluid has no residual magnetization and does not exhibit hysteresis.

Ferrofluids are well known in the art and various methods of preparing them are well known. As an example, the preparation of ferrofluids in an aqueous medium and the subsequent replacement of surfactant and redispersion of the particles in alternative carrier fluids such as oils, esters, and perfluorinated fluids is described in U.S. Pat. No. 3,917,538.

As mentioned above, these magnetizable fluids are used as the fluidizing fluid in the processes of the inventions disclosed herein. As also mentioned above, beds of nonmagnetic discrete particles levitated by the upward flow of a nonmagnetic fluid exhibit a well known regime termed fluidization in which the mixture of fluid and solids acquire the flowability properties of a fluid. The uniform equilibrium state of fluidization is normally unstable with respect to small disturbances thus accounting for the transition to a turbulent, agitated state. But when the bed particles are magnetizable and the fluidizing fluid is not, it has been shown that the equilibrium state may be preserved with application of an applied magnetic field; fluidizing velocities that are several times greater than the minimum fluidizing velocity ($U_{mf}$) may thus be accommodated by the system. See Rosensweig, R. E., Industrial and Engineering Fundamentals (1979), 18, 260–269 and Rosenweig, R. E., Science (1979), 204, 57–60.

In the present invention, the roles of magnetic and nonmagnetic phases are exchanged from that of the magnetically stabilized bed (MSB) mentioned above. Because these bed solids in the absence of the magnetic fluid are not magnetically attracted to each other, and the magnetic fluid retains its liquid property in the presence of an applied magnetic field it is unobvious that magnetic stabilization can be achieved. Experimentally, however, a bed of discrete nonmagnetizable particles is found to br stabilized when fluidized with the flow of a magnetizable liquid and subjected to a suitable applied magnetic field. By way of illustration, FIG. 1 shows the operating characteristics of a bed having a 25 centimeter initial length packed with 1 millimeter diameter glass beads in a column of 5 centimeters diameter. The bed is fluidized with a hydrocarbon base ferrofluid and subjected to a uniform, vertically oriented, 400 gauss applied field. Minimum fluidization velocity ($U_{mf}$) is detected from the break in either bed length or bed pressure drop versus flow rate. Transition velocity ($U_t$) marking the neutral stability curve is detected as the sudden onset of field fluctuations as the flow rate of the fluidizing fluid increases. The onset of field fluctuations coincides with the onset of bed length fluctuations and bed pressure drops fluctuations. The region between $U_{mf}$ and $U_t$ represents a quiescent, stabilized, fluidized regime. The region above line $U_t$ is an unstable and yet generally fluidized region. The region below $U_{mf}$ is the fixed bed region in which the fluid flows through the interstices between the bed solids without bed expansion.

Figure 2:
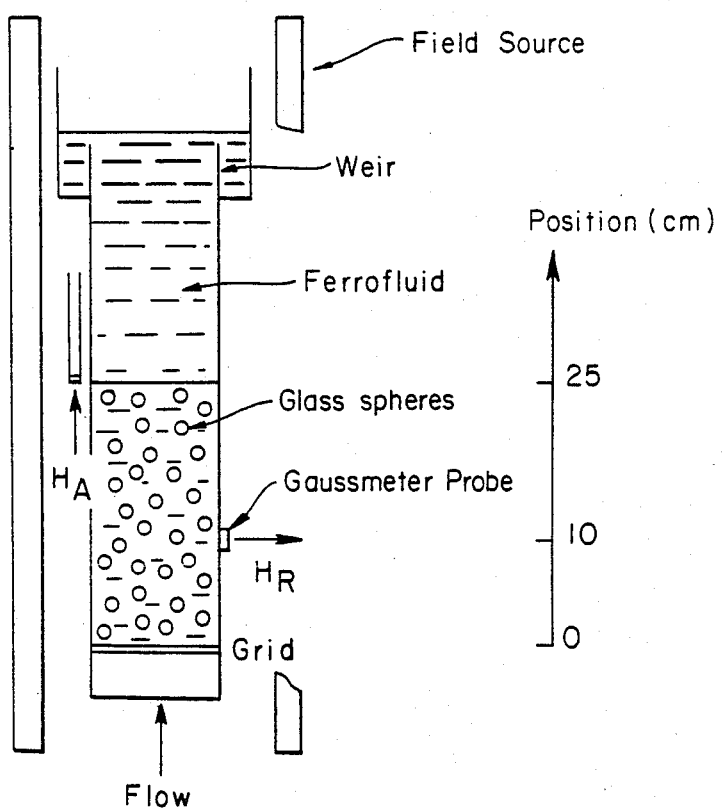
FIG. 2 schematically depicts a test apparatus used for the examples.

Ferrofluid is optically opaque and so prevents direct visual observation of the state of the bed. For the purposes of this invention, $U_t$ may be detected by measuring the component magnetic field transverse to the flow of the magnetizable fluidizing fluid with the applied magnetic field parallel to the flow of that fluid. FIG. 2 shows an experimental apparatus which may be used to determine the magnitude of various operational variables. This apparatus is a glass vessel having a grid located in its lower end and an overflow weir at its upper end so as to maintain a constant head of fluid within the bed area. Ferrofluid is introduced through the grid into the bed of enclosed glass spheres and overflows the weir after passage through the bed, then is recycled again through the grid. The flow rate of the recirculating ferrofluid is measured external to the bed. The magnetic field imposed axially on the bed is produced by a field source which surrounds the fluidizing vessel and itself is in the form of a cylindrical solenoidal electromagnet. The axial field ($H_a$) may be measured by a detector placed along side the vessel and the radial magnetic field ($H_r$) may be measured by a gaussmeter probe placed external to the bed as noted.

Figure 3:
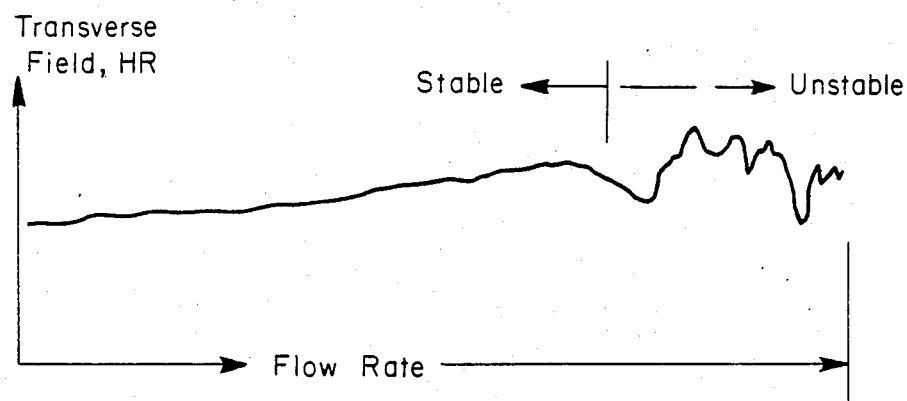
FIG. 3 shows the measured transverse magnetic field, as detected by the gaussmeter probe placed in the position shown in the experimental apparatus of FIG. 2, as a function of flow rate of the fluidizing fluid. This graph also shows the transition from stable to unstable operation in the fluidized bed as the flow rate of fluidizing fluid is increased at constant applied magnetic field intensity. The transition is detected as the onset of magnetic field fluctuations with time. Prior to transition the field increases somewhat as the bed expands.

FIG. 3 shows the relative magnitude of the transverse field $H_r$ as the flow is increased through the bed with all other variables remaining essentially constant. As the flow rate is increased past the value marked "stable", the bed begins to fluctuate as does the transverse magnetic field. As was shown in FIG. 1, the actual magnitude of the superficial velocity at $U_t$ varies as a function of the applied axial field. Consequently, a family of curves such as FIG. 3 furnishes the data needed to prepare the drawing shown in FIG. 1.

Figure 4:
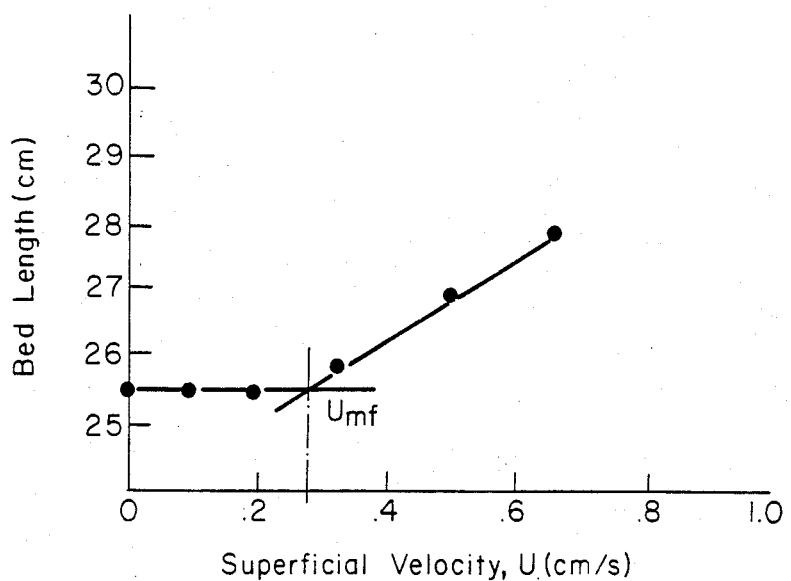
FIG. 4 shows bed length as a function of superficial velocity. Bed length was detected magnetically.
Figure 5:
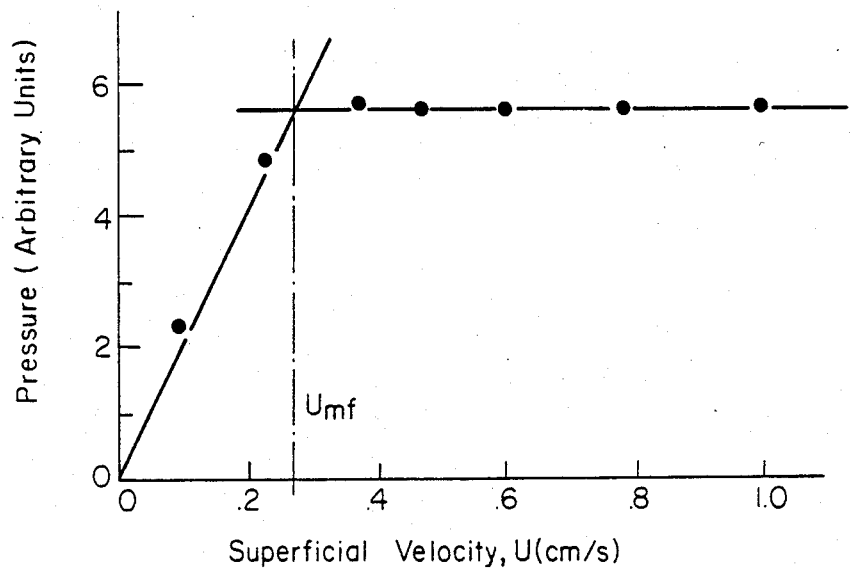
FIG. 5 shows a graph of pressure versus superficial velocity of the fluidizing medium within the fluidized bed.

As was mentioned above, the other end of the stable fluidization regime may be determined by detection of either the beginning of the bed expansion measured as a function of superficial velocity or by measurement of the pressure at various superficial velocities. FIGS. 4 and 5 are graphs of experimental data showing that $U_{mf}$ may be determined equally well by either method. It should be noted that in a magnetically stabilized bed utilizing nonmagnetizable fluidizing fluid and magnetizable bed solids, the incipient fluidization is not affected by the applied magnetic field intensity and the same is true here.

Having thus described the manner in which the inventive process generically operates, we will now describe a number of specific uses for the process.

One important use of the process of the instant invention comprises countercurrently feeding a hydrocarbon mixture to a bed of descending adsorbent particles under fluidization conditions wherein the bed is stabilized by application of a magnetic field, and recovering the separated hydrocarbon components.

The adsorbent particles are chosen to suit the particular feed to be treated and the substance that has to be removed from the feed. Inorganic (e.g., zeolites), organic, or high molecular weight organic (e.g., exchange resins) adsorbents may be used.

One class of adsorbents suited for the separation processes of the present invention include activated carbons, treated activated carbons, molecular sieve carbons; selected artificially synthesized zeolites, such as: "type A"; "type L"; "type X"; "type Y"; "type ZSM"; type beta; mordenite; faugasite; erionite; and the like; those zeolites which have particular silica-alumina ratios and those in which the original sodium or potassium cations are exchanged to other cations; silica-gels; particularly those which have particular steric properties related to the average pore diameter, specific surface area, pore volume and other parameters; selected activated alumina such as those having particular components of aluminum oxide and water, those hydrated forms, some particular crystal forms, and those which have a particular structure; activated clay or selected acid clays such as montmorillonite, exchanged halloysite or attapulgite.

Another class of macroreticular adsorbents include cation exchange resins with exchanged groups of benzene, sulfonic acid, carboxylic acid, phosphoric acid, strongly or weakly basic anion exchange resins, high molecular weight particles of styrene, divinylbenzene copolymer, or its halomethylated or cyanoethylated polymers; acrylonitrile cpolymers; high molecular weight compounds having several functional groups, such as cyano, cyano-methyl, chloromethyl, thioether, sulfone, isocyanate, thiocyanate, thiourea, allyl, acetylacetone, aldehyde, ketone, aliphatic, anhydride, ester, halogen, nitro and others.

Of the adsorbents discussed just above, the most suitable adsorbents for achieving high adsorption-desorption rates, selectivities, and capacities are synthetic zeolites, activated or treated carbon adsorbents, and high molecular weight organic materials.

Synthetic zeolites are one of the most useful inorganic adsorbents because the adsorption power of various molecules onto zeolites can easily be altered by exchanging the alkali metal, ammonium, or hydrogen ions, which usually come from the original production steps, with some other cations to change their electron configurations to the desired forms. Usually Group I metal ions, such as lithium, potassium, rubidium, cesium, silver, copper; Group II metal ions, such as beryllium, magnesium, calcium, strontium, barium, zinc, cadmium, mercury, titanium, vanadium, chromium, nickel, cobalt, iron, manganese, rare earth metals, uranium, lead cations or their mixtures are used to replace the alkali metals, ammonium, or hydrogen ions originally contained in the zeolites. Given a particular feedstream, the most suitable set of cations, their relative compositions, and the most effective activation treatments can be determined through experimentation, since cations-exchange procedures may be readily repeated many times. Generally, Type A synthetic zeolites are exchanged with calcium or magnesium or mixtures thereof for separating straight chain hydrocarbons from branched chain hydrocarbons. In processes for the separation of $C_8$ aromatic mixtures, and more particularly the separation of paraxylene from admixtures with its isomers or ethylbenzene Type X or Type Y crystalline aluminosilicate such as shown in U.S. Pat. Nos. 2,882,244 and 3,130,007 may be used. One particularly suitable adsorbent for the separation of a $C_8$ aromatic mixture is a potassium substituted Type Y zeolite having a unit cell of 24.5 to 24.75 Å, e.g., such as shown in U.S. Pat. No. 3,686,343, the disclosure of which is incorporated herein by reference.

Another quite desirable zeolite suitable for separation of ethylbenzene from feedstreams containing both ethylbenzene and a mixture of xylenes is zeolite beta. U.S. Pat. No. 3,793,385 suggests that paraxylene and ethylbenzene may be selectively adsorbed from mixtures comprising ethylbenzene and the isomeric xylenes using zeolite beta and toluene as a desorbent. The patent additionally suggests tha a large number of cations including lithium, potassium, cesium, magnesium, calcium, strontium, barium, and others may be ion-exchanged into the zeolite. The preferred method for adsorbing ethylbenzene from feedstreams containing both ethylbenzenes and xylenes is disclosed in U.S. Ser. No. 666,196, by Denise M. Barthomeuf, filed 10/29/84. Therein is shown a process using zeolite beta which has desirably been substituted with a large cation such as potassium, rubidium, or cesium. A particularly efficacious desorbent for ethylbenzene from the substituted zeolite beta is shown to be monoalkyl substituted benzene and paradialkylbenzene.

Zeolitic adsorbents typically are admixed with a binder which may be made of, for example, silica, alumina, or silica-alumina. The mixtures are then dried, calcined and sized. Suitable techniques for sizing and shaping the composite adsorbent are extrusion, prilling, beading, agglomeration, spray drying, etc. Polymeric adsorbents such as mentioned above are commercially available in many sizes and shapes. A similar situation exists for activated carbon adsorbents.

The nonmagnetizable particles have no critical size limitations. Obviously, larger particles may have poorer mass transfer characteristics and may be unsuitable for particular operations. Similarly, particles that are too small may not be suitable since they may be too reactive or subject to carryover in viscous fluidizing fluids or subject to agglomeration with each other. The particles should, however, be of such a size, dimension and shape as to be reasonably fluidizable in the reactor using the fluidizing fluid of choice.

The application of a magnetic field to the nonmagnetizable fluidizable bed particles in the adsorption or desorption zones in accordance with this invention is not limited to any specific method of producing the magnetic field. Conventional permanent magnets and/or electromagnets can be employed to provide the magnetic field used in the practice of the present invention. The positioning of the magnets will, of course, vary with the nonmagnetizable solids used, the magnetizable fluidizing fluid used, the saturation magnetization level of the magnetizable fluid, the degree of fluidization required, and the effects desired. In the preferred embodiments of the present invention, cylindrically wound electromagnets are employed to surround at least a portion of the fluidized bed to provide the most uniform magnetic field and consequently the best stability throughout the bed. As mentioned above, it is within contemplation of this invention that a magnetic field of varying strength be placed about the fluidization zone. This can be accomplished by use of discrete electromagnets employed at various axial locations about the fluidized bed, regulating the ampere-turns of the electromagnets. Electromagnets may be energized either by alternating or direct current, although direct current energized magnetic fields are preferred to maintain low operating voltages in large impedance electromagnets.

The process operating conditions to be employed in the practice of the present invention will vary and include those reaction conditions typically employed in adsorption-desorption hydrocarbon separation processes. These conditions will generally vary depending upon the hydrocarbon feedstream being treated, the adsorbent being used, etc. Although temperatures ranging from ambient to perhaps 400° C. and pressures ranging from about 1 to about 1600 psig may be used, since the feed generally must be in a liquid state, temperatures below about 250° C. are frequently desired. Similarly, because of the use of the liquid feed, equipment and energy means to pressurize is generally not of great concern. The relative interstitial velocity of the fluidizing fluid, which contains the hydrocarbon feed to be treated in addition to the material rendering that fluid magnetizable, may range from about 0.01 to about 3 cm/sec, more preferably from about 0.1 cm/sec to about 2 cm/sec. The bed particles preferably move countercurrently in a plug flow manner against the ascending feed by the action of gravity in the contacting vessel. The bed solids circulation rate may vary widely depending on the concentration of the component in the feed to be adsorbed, the flow rate of the feedstream, the flow rate of the desorbents, etc.

The hydrocarbon feed mixture applicable to this variation of the present invention may be made up of a mixture of 2 or more hydrocarbon components having from 3 to 30 carbon atoms per molecule. Examples of these hydrocarbon components are propane, butane, pentane, hexane, heptane, octane, nonane, decane, dimethylbutane, dimethylpentane, and other normal aliphatic hydrocarbons and their isomers; cyclohexane, decaline, tetraline and other alicyclic-hydrocarbons; benzene, toluene, ortho-, meta-, and para-xylene, diethylbenzene, ethyltoluene; trimethylbenzene, butylbenzene and other aromatic hydrocarbons, such as alkylbenzene, or alkylnaphthalene; refinery products comprising mixtures of paraffins, naphtha or reformate; other hydrocarbon derivatives from naphtha cracking processes and those processes yielded from distillation, alkylation, or hydrogenation processes. Both hydrocarbon mixtures comprising two or more compounds of different molecule weights, as well as the same molecular weights, that is, isomers, are included as feed mixtures. Examples of isomeric mixtures are $C_5$ aliphatic isomers of dimethylpropane and pentane; $C_6$ aliphatic isomers of dimethylbutane, ethylbutane, methylpentane and hexane; $C_7$ aliphatic isomers of dimethylpentane, methylhexane and heptane; $C_8$ aliphatic isomers of trimethylhexane and octane, $C_8$ alicyclic isomers of dimethylcyclohexane and ethylcyclohexane. The process of the present invention may be used for separating straight chaing paraffins from recycle streams in $C_5/C_6$ recycle isomerization units. Another feed suited for the process of the present invention is a $C_9/C_{18}$ hydrocarbon fraction and more preferably the $C_{10}/C_{15}$ kerosene fraction. Feedstreams may contain normal paraffins, isoparaffins and aromatics in varying concentrations, depending on the type of crude which the hydrocarbon fraction is derived and the carbon number range of that fraction.

As noted above, this process is especially suitable for the difficult separation of various $C_8$ aromatic constituents, such as ethylbenzene, paraxylene, orthoxylene, and metaxylene, one from the other.

The adsorption may take place in any suitable vessel. The vessel may be equipped with internal supports, feed distribution means, etc. Bed solids will be introduced to the top of the vessel, and in the lower portion of the adsorption vessel, there will be disposed a suitable grid means for distributing magnetizable desorbent liquid. Liquid raffinate is withdrawn from the upper portion of the bed above the feed but below the point where bed solids are added. The center portion of the vessel will have means for distributing the incoming hydrocarbon feed. The bottom or lower portion of the adsorption vessel will have means for removing spent solids from the adsorption vessel. This opening may be on the side of the vessel or at its bottom. A pipe grid may be utilized to introduce the hydrocarbon feed and magnetizable liquid into the vessel. By use of a pipe grid, the spent solids may flow past the feed grid by gravity to the regenerator or desorber. It may be desirable in some instances to incorporate a solids-free zone beneath a particular fluidized portion of the bed such as that disclosed in U.S. Ser. No. 6/669,899, by Wei-Kuo Lee, filed 11/9/84, the entirety of which is incorporated herein by reference. Finally, extract product is removed from the lower portion of the bed at a point below the feed but above the point where solids are discharged or magnetic fluid desorbent is introduced.

Figure 6:
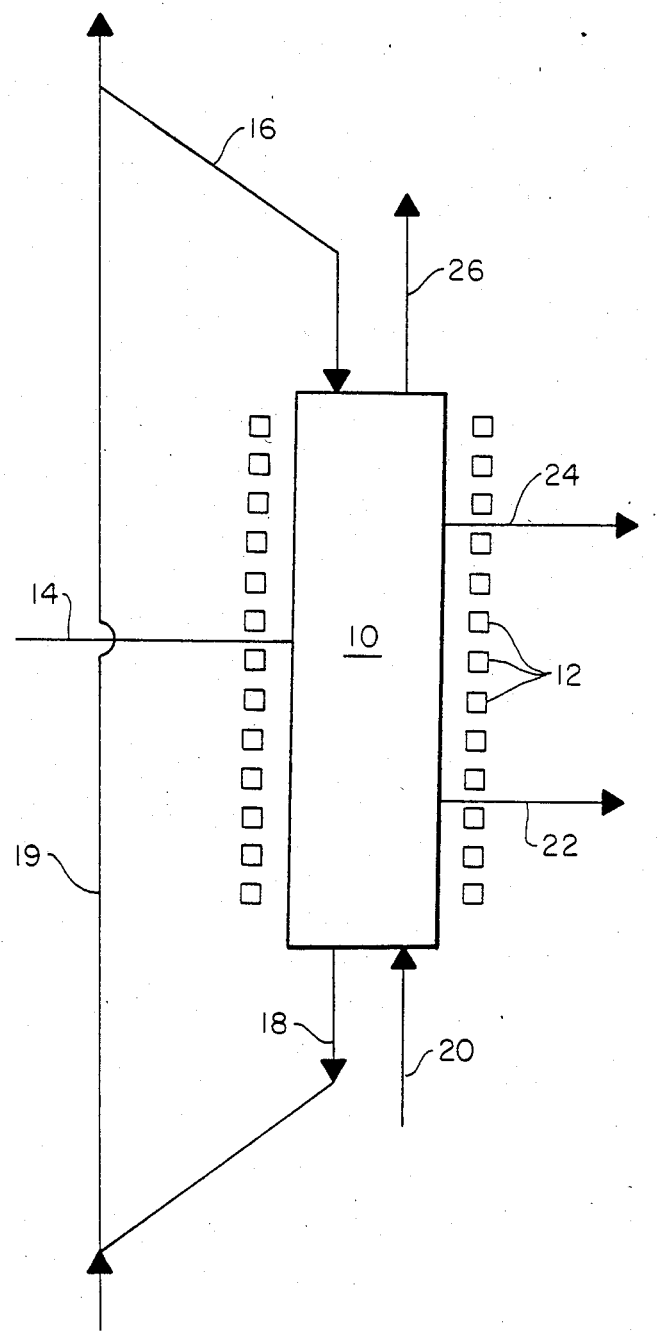
FIG. 6 is a schematic portrayal of an adsorption column used for separating at least two components of a hydrocarbon mixture.

A specific generalized example of this variation of the present invention is shown in FIG. 6. Within the contacting vessel a bed of nonmagnetizable particles comprising a molecular sieve is contacted with a liquid feed comprising two or more types of hydrocarbons within the magnetically stabilized adsorption zone. In FIG. 6, a fluidization vessel 10 having a series of solenoidal electromagnets 12 disposed about its outer periphery is shown. No vessel internals are indicated to allow for ease of explanation. The hydrocarbon feedstream is introduced into vessel 10 through line 14. The hydrocarbon feedstream is innoculated with a material, e.g., 100 Å magnetite, in an amount sufficient to render the hydrocarbon stream magnetizable and itself, a ferrofluid. For the purposes of illustration, this hydrocarbon feedstream is made up of two components, A & B, one of which is preferentially adsorbed in a zeolitic adsorbent introduced into vessel 10 through line 16. The adsorbent leaves the vessel 10. A recycle line 19 having a lift fluid may be used if desired. In this preferred embodiment, a desorbent, which is also innoculated with a material, e.g., 100 Å magnetite, and itself a ferrofluid, is introduced into the vessel through line 20. The desorbent has the function of desorbing the hydrocarbon A from the adsorbent within the lower region of the vessel 10. This allows removal of a mixture of hydrocarbon A with some desorbent as the extract through line 22. A mixture of hydrocarbon B and some desorbent is removed as the raffinate through line 24. The remaining desorbent is removed through line 26. The mixtures in lines 22 and 24 may be separated by, e.g., distillation, to produce pure components, hydrocarbons A and B as well as a desorbent suitable for recycle to line 20.

The colloidal magnetic particles may be removed with the bottom streams produced upon distillation of the two product streams and recycled.

By use of a magnetically stabilized bed, it is possible to use smaller bed particles than in fixed bed processes. This is desirable because the use of smaller particles significantly reduces overall mass transfer or diffusion resistance. In a fixed bed system, pressure drop is inversely proportional to particle size, as can be predicted by the Ergun equation, a well known correlation of flow through fixed beds (S. Ergun, Chemical Engineering Progress, Vol. 48, p. 89 (1952)). Plugging due to fines capture further increases the pressure drop. Thus, in fixed beds, because of the excessive drop, it is impractical to improve mass transport by reducing particle size. In a magnetically stabilized bed, on the other hand, the pressure drop is constant and independent of particle size, being equal to the weight of the bed divided by the vessel cross-sectional area. Faster mass transfer rates can be obtained by reducing particle size. Faster means transfer rates in a magnetically stabilized bed of smaller particles will decrease the size of an adsorption bed compared to that of a fixed bed of conventionally sized particles. Equivalently, a large number of theoretical contacting stages may be obtained within a short length of adsorption bed.

The stable bed contacting technique of this invention is not, of course, limited to countercurrent operation with a solids feed and removal in a single vessel. It is just as applicable, for example, to a batch bed operation or to cocurrent solids operation with liquid and solids upflow in a vertical vessel.

Furthermore, the disclosed process is suitable for the catalytic reaction of one or more fluid feeds in the stabilized fluidized bed wherein the nonmagnetizable but fluidizable particles comprise solid heterogeneous catalyst for the reaction of those materials. The reaction product may be gaseous, although such a product may disturb the fluidization equilibrium of the MSB. Preferably the products are liquid and maintain the stability of the bed. If the liquids are immiscible they may be separated by known means and processes from the effluent of the bed.

Finally, this process may be used in crossflow operations, such as those shown in U.S. Pat. No. 4,443,231 to Siegell, issued Apr. 17, 1984. The adsorbents which may be used in such a cross-flow bed are the same or similar to those described above. The nonmagnetizable bed particles in such a process continuously move transverse to the flow of the magnetizable carrier fluid, which serves to fluidize the bed, such that components of an injected feed mixture are transported downstream with the solids at varying distances from the injection point depending upon the adsorption and desorption characteristics of the components. Product streams comprising a portion of the carrier fluid and a portion of the feed mixture containing at least a portion, preferably a major portion, of one of the components can then be recovered from the stream issuing from the surface of the bed, the most strongly adsorbed component being transported and thus recovered farthest from the injected point. By proper selection of ferrofluid colloidal concentration, magnetic field strengths, localized velocity, etc., the solids will move in near plug flow across the path of the ascending fluidizing fluid.

This invention will be further understood by reference to the following example which is not intended to restrict the scope of the claims appended hereto.

EXAMPLE 1

An equal mixture of metaxylene and ethylbenzene will be mixed with a concentrated ferrofluid to yield a magnetizable fluid having saturation magnetization of about 250 gauss. This mixture is fed to a magnetically stabilized fluidized bed containing a beta zeolite. The beta zeolite passes in countercurrent flow to the mixture of metaxylene, ethylbenzene, and a colloidal magnetite. Ethylbenzene is preferably adsorbed. A magnetizable desorbent comprising, for example, dialkylbenzene and 5 volume percent 100 Å magnetite is introduced at the bottom of the bed, while the liquid comprising ethylbenzene and desorbent is removed at a level above the bottom but below the feed point in the bed. The desorbent will effectively displace the ethylbenzene from the zeolite as the desorbent passes upwardly through the lowest zone of the MSB and consequently the liquid leaving the MSB as extract product is a mixture of desorbent and ethylbenzene. Between the feedpoint and the raffinate withdrawal point, the fluid of the column contains ethylbenzene and metaxylene in mixture with dialkylbenzene and magnetic particles. The descending solids stream of beta zeolite selectively adsorbs ethylbenzene and transports the ethylbenzene down the column. Above the raffinate withdrawal point, the upward moving fluid stream contains metaxylene, dialkylbenzene, and magnetic particles. The descending beta zeolite adsorbs metaxylene from this stream so that the desorbent stream leaving the top of the column is sufficiently free of metaxylene so that it can be recycled to the bottom of the column. Product streams of desorbent plus metaxylene and desorbent plus ethylbenzene are sent to distillation towers. The ferrofluid will remain in the bottom stream of each tower. The magnetizable desorbent may be recycled to the adsorption process, e.g., introduced at the bottom of the bed or mixed with the feedstream or both.

It is apparent that various modifications and changes can be made in the conditions of operations and the like without departing from the spirit and scope of the invention claimed below.

We claim as our invention:

1. The process for stabilizing a fluidized bed consisting essentially of solid non-magnetizable solid particles having a substantially vertical axis and comprising the steps of:

fluidizing the non-magnetizable particles using a magnetizable liquid flowing upwardly through said bed at a superficial velocity between $U_{mf}$ and $U_t$, and subjecting the bed to a substantially uniform applied magnetic field having a substantial component along the axis of the bed, said field being of a strength sufficient to prevent substantial particle backmixing along said axis.

2. The process of claim 1 wherein the nonmagnetizable particles comprise zeolites.

3. The process of claim 2 wherein the nonmagnetizable particles comprise zeolites and a binder.

4. The process of claim 2 wherein the zeolites are selected from the group consisting of Type X, Type Y, Type A and Type beta.

5. The process of claim 1 wherein the magnetizable fluid comprises a ferrofluid.

6. The process of claim 5 wherein the magnetizable fluid additionally comprises a hydrocarbon.

7. The process of claim 6 wherein the hydrocarbon comprises an aromatic hydrocarbon.

8. The process of claim 7 wherein the aromatic hydrocarbon comprises ethylbenzene and isomeric xylenes.

9. The process of claim 1 wherein the magnetizable fluid is in countercurrent flow with respect to the nonmagnetizable particles.

10. The process of claim 1 wherein the magnetizable fluid flows cocurrently with the non-magnetizable particles comprising the bed.

11. The process of claim 1 wherein the bed is a nonmoving fluidized bed.

12. The process of claim 1 wherein the non-magnetizable particles move across the flow of the magnetizable fluid.

* * * * *